United States Patent [19]
Quisno

[11] Patent Number: 4,788,971
[45] Date of Patent: Dec. 6, 1988

[54] PATCH SYSTEM FOR USE ON THE SKIN

[75] Inventor: Robert A. Quisno, Monroe, Ohio

[73] Assignee: Hill Top Research, Inc., Cincinnati, Ohio

[21] Appl. No.: 72,626

[22] Filed: Jul. 13, 1987

[51] Int. Cl.$^4$ .............................................. A61B 10/00
[52] U.S. Cl. .................................... 128/743; 604/289
[58] Field of Search ............... 128/632, 636, 743, 760, 128/630, 132 R, 153–156, 165; 604/289, 307, 312, 310, 46–47, 332

[56] References Cited

U.S. PATENT DOCUMENTS

| | | | |
|---|---|---|---|
| 4,158,359 | 6/1979 | Kurokawa et al. | 128/630 |
| 4,190,060 | 2/1980 | Greenleaf et al. | 604/312 X |
| 4,323,557 | 4/1982 | Rosso et al. | 604/307 X |
| 4,450,844 | 5/1984 | Quisno | 128/743 |
| 4,542,751 | 9/1985 | Webster | 604/312 X |

FOREIGN PATENT DOCUMENTS

| | | | |
|---|---|---|---|
| 8100199 | 2/1981 | European Pat. Off. | 128/743 |
| 0205974 | 12/1986 | European Pat. Off. | 604/289 |
| 2420345 | 11/1975 | Fed. Rep. of Germany | 128/743 |
| 3040544 | 5/1982 | Fed. Rep. of Germany | 128/672 |

OTHER PUBLICATIONS

Phillips, "An Improved Adhesive Patch for Long-Term Collection of Sweat", Biohat., Med. Dev., Art. Org., 8(1), 13–21, (1980).

Primary Examiner—Kyle L. Howell
Assistant Examiner—Angela D. Sykes
Attorney, Agent, or Firm—Frost & Jacobs

[57] ABSTRACT

A patch system for use on the skin of a human or animal subject for predictive testing, diagnostic testing and to serve as a dermal delivery system for drugs. The patch system comprises an open, one-piece, inverted dish-shaped housing of non-toxic, inert, soft and flexible material. About its periphery the housing terminates in at least one and preferably a pair of parallel, spaced, continuous, skin-contacting edges. The housing may contain an absorbent pad. About its periphery and spaced slightly upwardly from the one or more skin-contacting edges, the housing has a planar flange extending outwardly from its exterior surface. The bottom surface of the flange is adhesive coated. The adhesive coated flange affixes the housing to the skin. Prior to use, the housing and its peripheral flange may be provided with a protective release paper.

16 Claims, 3 Drawing Sheets

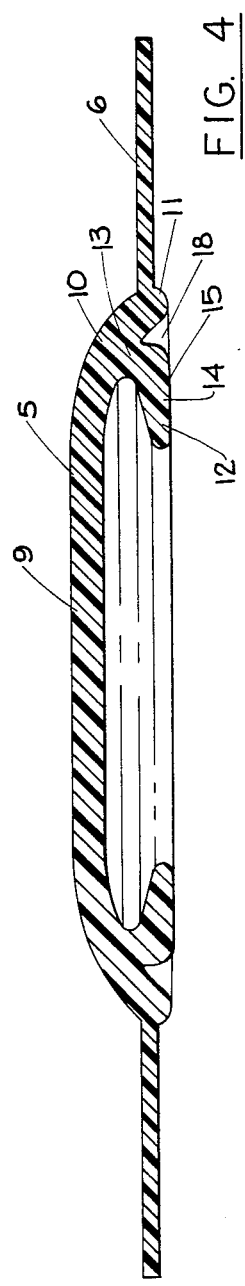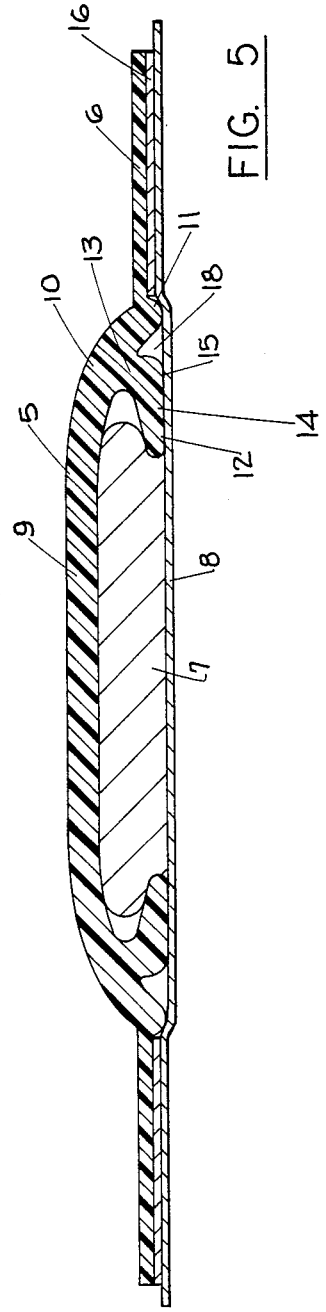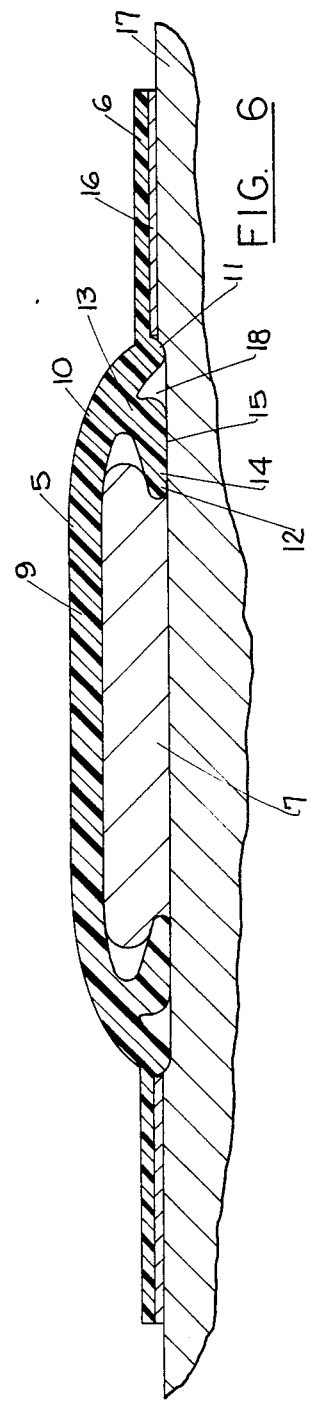

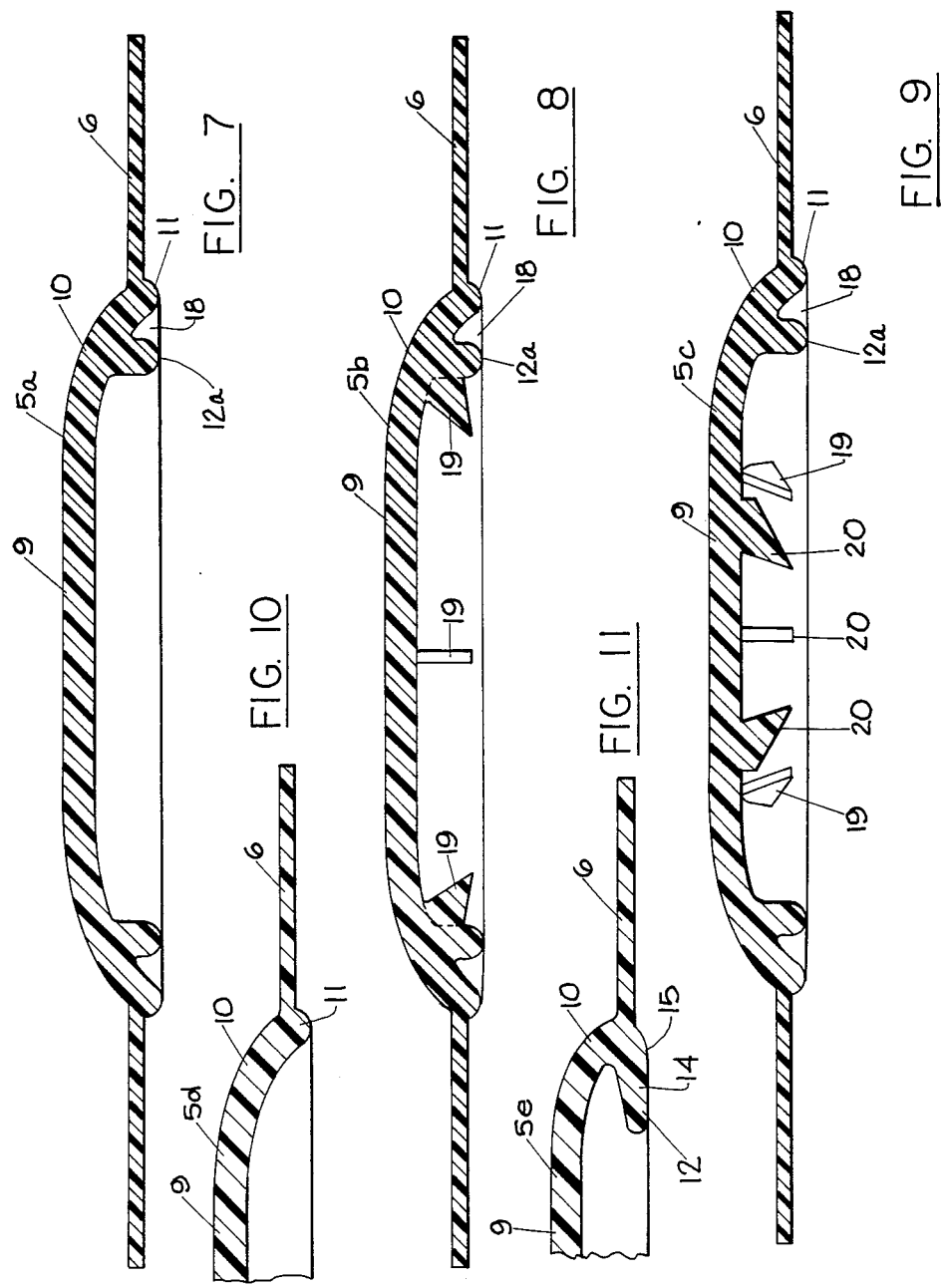

PATCH SYSTEM FOR USE ON THE SKIN

TECHNICAL FIELD

This invention relates to a patch system for use on the skin of a human or animal subject, and more particularly to a patch system utilizing an open, one-piece, inverted dish-shaped housing of non-toxic, inert, soft and flexible material, terminating at its periphery in at least one integral, continuous, skin-contacting edge, and having an integral, peripheral flange with an adhesive coated underside for adhering the housing to the skin.

BACKGROUND ART

Prior art workers have devised numerous types of patch systems. In their simplest form, prior art patch systems comprised absorbent patches of woven or non-woven synthetic or natural fibers affixed directly to an adhesive tape and, in many instances, protected by release papers. In similar structures, an impervious layer of cellophane, or the like, was located between the patch and the adhesive tape. In many of these prior art structures, the sample material applied to the patch system came into contact with the tape. Many of these systems were limited as to the type of tape which could be used and frequently, the tape would not adhere well, particularly in the presence of water, perspiration, or the like. Often the tape was more irritating and would gap easily so that the patch system was non-occlusive. The sample material applied to such structures would frequently dry out rapidly.

In an attempt to provide a more occlusive patch system and to prevent the sample from being in contact with the tape, prior art workers have developed various types of small, dish-like housings having a continuous skin-contacting edge. These housings have generally been made of metal such as aluminum and the like. These structures, however, have been characterized by certain disadvantages such as being rigid, too thick and having limited sample volume. A recent example of such structures is taught in U.S. Pat. No. 4,158,359. This patent teaches a single or multi-piece housing containing an absorbent pad and having peripheral edges which are turned inwardly or outwardly so as to form a continuous seal with the skin. One embodiment of this patent comprises a housing having outwardly rolled edges with an additional annular member adapted to form a second seal and to retain an absorbent pad within the housing. The housing of this patent is affixed to an adhesive covering sheet and is surrounded by an annular porous protecting sheet. The housing of this reference has a limited sample volume and is generally rigid, being made of metal or a synthetic resin.

U.S. Pat. No. 4,450,844 is directed to a patch system which overcomes the above noted deficiencies of earlier prior art patch systems and which is substantially completely occlusive to render tests, for example, more sensitive and reproducible. This is accomplished by means of a pair of integral, parallel, spaced, continuous, skin-contacting edges of the housing having an air space therebetween, and by virtue of the fact that the housing is made of soft and flexible material.

The sample material applied by way of the patch system of U.S. Pat. No. 4,450,844 does not contact the adhesive of the tape which mounts the housing and different types of tape can be used, such as hypo-allergenic tapes. The housing, which is made of non-toxic, inert material, provides good sample retention indefinitely and can be used with or without an absorbent pad. Various sizes of housings and absorbent pads can be used and the system permits modifications of patch testing procedures not possible with earlier prior art systems.

The patch system of U.S. Pat. No. 4,450,844 works well even in the presence of perspiration and one to whom the patch system is applied can swim and shower. When used for test purposes, the patch system (with sample applied) can be prepared ahead of time, in the laboratory and taken to the test site, ready for use. This patch system provides a technique which may reduce the number of visits for panelists during testing. The system further enables measurement of the amount of sample before and after application to a panelist, which is useful in controlled investigations of new drugs. Finally, the system can be used as single patches or made into strips containing a plurality of housings.

The present invention is based upon the discovery that the patch system of U.S. Pat. No. 4,450,844 can be markedly improved by providing the housing with a planar flange about its periphery, spaced slightly above the one or more skin-contacting edges of the housing. The flange extends outwardly from the exterior surface of the housing and is provided with a layer of adhesive on its bottom surface so that the flange is used to adhere the housing to the skin. Prior to use, the housing and its peripheral flange may be provided with a protective release paper.

The improved system eliminates the need of a cover sheet in the form of an adhesive coated tape to affix the housing to the skin. It is less expensive to manufacture and is easier to manipulate. Channeling is substantially reduced or eliminated. Finally, the patch system of the present invention has an aesthetically more pleasing appearance.

The patch system of the present invention has numerous applications. For example, it can be used in conventional predictive patch testing and in diagnostic testing (for example, by dermatologists and allergists to determine what is the causative agent for a patient's skin reaction). The patch system can also be used as a dermal drug delivery vehicle. The housing will hold a sufficient quantity of drug to allow the drug to be gradually absorbed through the skin for certain treatments such as an anesthetic patch for a painful procedure. The patch system is suitable for use both with humans and animals.

DISCLOSURE OF THE INVENTION

According to the invention there is provided a patch system for use on the skin of a human or animal subject for predictive testing, diagnostic testing, drug delivery and the like.

The patch system comprises an open, one-piece, inverted dish-shaped housing of non-toxic, inert, soft and flexible material. At its periphery, the housing terminates in at least one continuous, skin-contacting edge. About the periphery of the housing and spaced slightly upwardly from the at least one skin-contacting edge is a planar flange extending outwardly from the exterior surface of the housing. The flange carries a layer of adhesive on its bottom surface and comprises means to affix the housing to the skin. The housing may contain an absorbent pad, if desired.

In a preferred embodiment of the present invention, the housing terminates in a pair of integral parallel, spaced, continuous, skin-contacting edges. The outer skin-contacting edge of the housing is beaded or rounded, providing a rounded sealing surface. The inner edge is flattened and provided with an annular flange-like portion extending inwardly of the housing so as to provide a wide, flat sealing surface. The sealing surfaces of both the inner and outer edges are substantially coplanar. The annular flange-like portion of the inner edge also serves as a retaining means for an absorbent pad, if used.

In a second embodiment, both the inner and outer edges are beaded or rounded, providing rounded, substantially coplanar sealing surfaces. A third embodiment differs from the second embodiments only in that a plurality of inwardly extending spikes are provided in association with the inner edge, evenly spaced thereabout, to retain an absorbent pad with the housing. A fourth embodiment is similar to the third embodiment, differing only in that additional inwardly extending spikes are provided on the inside surface of the housing, itself, spaced inwardly from the inner edge and its associated spikes, to further assist in retaining an absorbent pad with the housing.

In a final embodiment, the housing terminates in a single, continuous, skin-contacting edge. This edge may be a simple beaded or rounded edge, or it may be flattened and provided with an annular flange-like portion extending inwardly of the housing.

While each embodiment of the housing may be used with or without an absorbent pad, it will be affixed to the skin by the adhesive-coated, planar, outwardly extending flange which is peripherally continuous and is preferably a one-piece, integral part of the housing. Prior to use, the adhesive-coated flange and the housing of the patch system may be protected with a removable release paper.

BRIEF DESCRIPTION OF THE DRAWINGS

FIG. 4 is a cross sectional view taken along section line 4—4 of FIG. 3.

FIG. 5 is a cross sectional view similar to FIG. 4 and illustrating the housing thereof provided with an absorbent pad, an adhesive layer on its outwardly extending flange and a protective release paper.

FIG. 6 is a cross sectional view illustrating the structure of FIG. 5 with its release paper removed and the housing mounted on the skin of a subject.

FIG. 7 is a cross sectional view of another embodiment of the housing of the present invention.

FIG. 8 is a cross sectional view of another embodiment of the housing of the present invention.

FIG. 9 is a cross sectional view of yet another embodiment of the housing of the present invention.

FIGS. 10 and 11 are fragmentary, cross sectional views illustrating the present invention applied to housings having a single, continuous, skin-contacting edge.

DETAILED DESCRIPTION OF THE INVENTION

Figure 1:
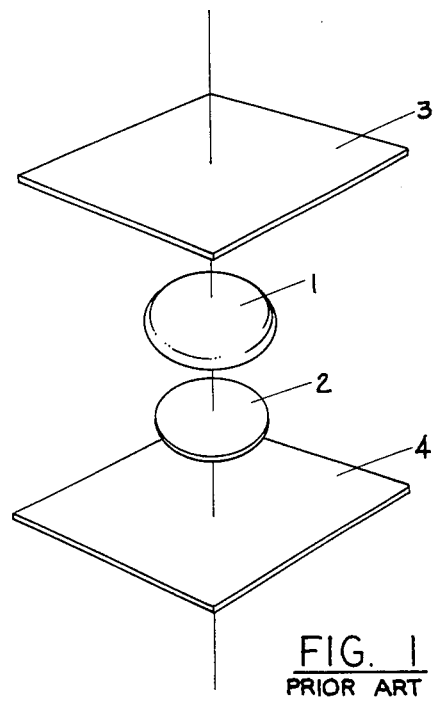
FIG. 1 is an exploded perspective view of the prior art patch system of U.S. Pat. No. 4,450,844.

Reference is first made to FIG. 1 wherein the prior art patch system of U.S. Pat. No. 4,450,844 is illustrated in its most complete form. That patch system comprises a sample-retaining housing 1 and an absorbent pad 2, adapted to be mounted in the housing 1. In most applications, the housing 1 is retained in position on the skin by an adhesive coated cover sheet 3. Prior to use, the housing 1, absorbent pad 2 and cover sheet 3 are protected by a release paper 4.

Figure 2:
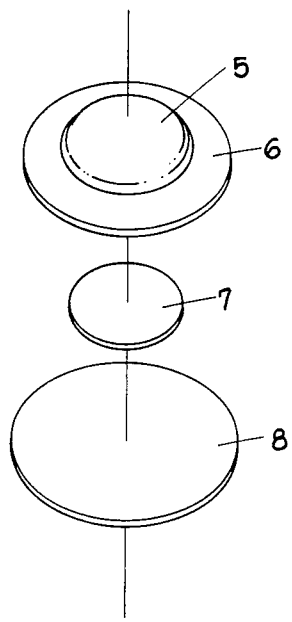
FIG. 2 is an exploded perspective view of the patch system of the present invention.

FIG. 2 is an exploded view, similar to FIG. 1, but illustrating the patch system of the present invention. The system of the present invention comprises a sample-retaining housing 5 having a planar outwardly extending flange 6. The underside or bottom of flange 6 is provided with an adhesive (as will be described hereinafter) by which the housing 5 is affixed to the skin. An absorbent pad 7 may be included in the system, if desired. A protective release paper 8 is provided to protect the housing 5, absorbent pad 7 and flange 6.

The housing 5, like housing 1, can be made of any appropriate soft and flexible material which is substantially non-toxic and inert. The housing 5 lends itself well to being molded of a plastic material. For example, the polyethylene vinyl acetate group of plastics can be used. As a non-limiting example, excellent results have been achived with U.E. 634-00 Ethylene vinyl acetate copolymer, sold under the trademark Ultrathene by United States Industrial Chemicals of Cincinnati, Ohio. This material is inert, very pure, non-toxic, contains no plasticizers and demonstrates no tendency to be leachable. The flange 6 preferably comprises an integral, one-piece part of housing 5.

As is true of the absorbent pad 2 of FIG. 1, the pad 7 may be made of an appropriate material safe for use adjacent to the skin and compatible with the sample to be applied to the pad. With these limitations in mind, the pad may be made of a spongy or foamed plastic material, paper, or woven or nonwoven synthetic or natural fibers. Excellent results have been achieved, for example, with a nonwoven cotton swatch sold under the trademark Webril by Kendall Company of Wellesley Hill, Mass.

The samples or drugs to be applied to the skin by means of the patch system of the present invention may be in various forms such as liquids, solids, pastes, and powders. In the case of solids, semi-solids, powders and the like, it may be desirable to dispense with the absorbent pad 7, filling the housing 5 directly with the sample.

In the prior art embodiment of FIG. 1, the cover sheet 3 is normally made of a tape, coated on one side with a pressure-sensitive adhesive. The cover sheet 3 may be made of any appropriate adhesive tape which is non-irritating to the skin. Selection of an appropriate adhesive tape is made on the basis of the nature and purpose of the application of the patch system and the conditions thereof. For example, the tape can be a plastic film tape, a fabric tape, a paper tape, or the like. It has been found, however, that tapes tend to wrinkle, forming channels therein.

In the embodiment of FIG. 2, according to the present invention, the tape cover sheet 3 is eliminated and replaced by flange 6 constituting an integral part of housing 5. The underside or bottom of flange 6 is coated with an appropriate pressure-sensitive adhesive, non-irritating to the skin. Elimination of cover sheet 3 not only improves the aesthetics of the system, but also reduces the cost of manufacture and the number of assembly steps. Furthermore, the flange 6 virtually eliminates problems of channeling and the like.

The release paper 8 (as is true of release paper 4 of FIG. 1) can be of any appropriate type, suitable for use with the particular application to which the patch system is directed. Excellent results have been achieved, for example, utilizing a paper coated with polyethylene silicone or an aluminum foil. A specific example is 63# BL Polysilk ® L275, sold by H. P. Smith Paper Company of Chicago, Ill.

Figure 3:
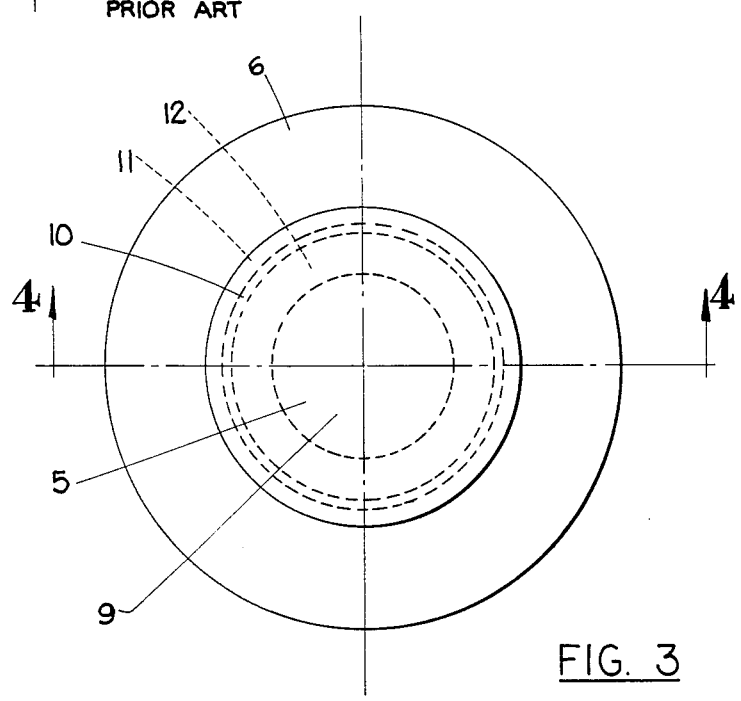
FIG. 3 is a top plan view of the housing of FIG. 2.

Reference is now made to FIGS. 3, 4 and 5 which illustrate the preferred embodiment of the housing 5. The housing 5 comprises an integral, one-piece, molded structure of an inverted, circular, dish-shaped configuration. The housing has a substantially planar central body portion 9. Near its periphery, the housing 5 has a portion 10 which curves downwardly and outwardly. The portion 10 terminates in a beaded or rounded edge 11. The rounded edge 11 constitutes the outer skin-contacting edge. A second or inner skin-contacting edge is indicated at 12. The skin-contacting edge 12 comprises a first portion 13 which depends downwardly from the inner surface of the curved portion 6. The portion 13 terminates in a laterally and inwardly extending, annular flange-like portion 14. As can be seen in FIG. 5, the flange-like portion 14 serves as a retaining means for the absorbent pad 2 (when used). The annular flange-like portion 14 also provides a surface 15 constituting a skin-contacting and sealing surface. It will be apparent from FIG. 4 that the portion of the outer edge 11 which contacts the skin and the surface 15 of the inner edge 12 are substantially coplanar. It has been found that the housing 5, by virtue of its soft and flexible nature and its outer skin-contacting edge 11 and inner skin-contact edge 12, provides a patch system of excellent occlusive properties.

As is clearly shown in FIG. 4, the housing flange 6 preferably comprises an integral, one-piece part of the molded housing 5. It will be noted from FIG. 4 that flange 6 is substantially planar and is parallel to the plane in which the skin-contacting edges 11 and 12 lie, being spaced slightly upwardly therefrom. This slight upward spacing of flange 6 from the skin-contacting surfaces 11 and 15 assures that the flange 6 will in no way interfere with the achievement of good contact between surfaces 11 and 15 and the skin.

The width of flange 6, as measured from the exterior surface of housing 5 to the peripheral edge of flange 6, does not constitute a limitation of the present invention. It has been found that excellent results are achieved when the width of flange 6 is approximately one-third the diameter of housing 5. This, of course, can vary, depending upon the size of the housing 5 used. In an exemplary, but non-limiting example, housings 5 were molded having a diameter of 0.75 inch (19.05 mm). The flange 6 had a width of 0.25 inch (6.35 mm), thus giving the overall structure a diameter of 1.25 inches (31.75 mm).

It will further be noted from FIG. 4 that the thickness of flange 6 is considerably less than the thickness of housing 5. While the thickness of flange 6 does not constitute a limitation of the present invention, in the non-limiting example given above, housings were molded having a wall thickness of from about 0.035 inch to about 0.040 inch (from about 0.88 mm to about 1.01 mm), and the flanges thereof had a thickness of about 0.015 inch (0.38 mm).

FIG. 5 illustrates the preferred embodiment of the present invention in complete form. As indicated above, depending upon the nature of the use of the system and the sample contained therewithin, the pad 7 may be eliminated. In FIG. 5 the flange 6 is illustrated as being provided with a layer of appropriate pressure-sensitive adhesive 16. For purposes of illustration, it will be understood that the adhesive layer 16 is exaggerated in thickness.

In FIG. 5, the release paper 8 is shown mounted in place. In FIGS. 2–5, the chamber 5, the flange 6, the pad 7 and the release paper 8 are all shown as being circular in configuration. Release paper 8 preferably has a diameter slightly greater than the diameter of flange 6 with an edge of the release paper 8 extending beyond the edge of the flange 6, so that the release paper can be easily engaged and removed from the housing 5 and its flange 6. It would be within the scope of the invention to make release paper 8 and flange 6 substantially coextensive, with only a small peripheral portion of release paper 8 extending beyond the peripheral edge of flange 6 in the form of a tab or the like for easy removal of the release paper.

The embodiment of housing 5 and its flange 6 illustrated in FIGS. 2 through 5, and those embodiments to be described hereinafter and illustrated in FIGS. 7 through 11 have been shown as having an overall circular configuration. While this configuration is preferred, the housing 5 and flange 6 are not intended to be so limited. The housing 5 and flange 6 could have an overall configuration which is square, rectangular, triangular, hexagonal or the like. So long as the structure is made of soft and flexible material and is provided with at least one (and preferably two) continuous, skin-contacting edge or edges, as taught herein, the improved characteristics of the present invention will be achieved.

Reference is now made to FIG. 6 wherein the embodiment of FIGS. 2 through 5 is shown applied to the skin, generally indicated at 17. In use, the release paper 8 is removed and the sample to be administered or tested is applied to the absorbent pad 7. As indicated above, under some circumstances the sample is applied directly to the housing 5, the pad 7 being eliminated. Once the sample has been applied to the patch system, the patch system is applied directly to the surface of the skin 17. Again, it will be remembered that the sample can be applied to the patch system ahead of time and a release paper applied. The release paper is thereafter removed at the time of use.

It will be evident from FIG. 6 that the body portion 9 of the housing 5 is spaced from the skin 17 by the curved portion 10 and skin-engaging edges 11 and 12. The sample is maintained out of contact with the flange 6 by the housing 5. Furthermore, the housing 5 assures that the flange 6 and its adhesive layer 16 contact the skin at an adequately spaced distance from the area of contact between the skin and the sample. The spacing of the flange 6 in a plane parallel to and slightly above the plane of skin-engaging edges 11 and 12 assures that edges 11 and 12 form a good, continuous seal with the skin 17. A highly occlusive structure is achieved by virtue of the soft and flexible nature of housing 5 and the two continuous peripheral sealing edges 11 and 12 with an air space 18 therebetween.

A second embodiment of the housing of the present invention is illustrated in FIG. 7. In this figure, the housing is indicated at 5a. The housing 5a is substantially identical to the housing 5 of FIGS. 2 through 5, with the exception of the configuration of the inner sealing edge. As a result of this, like parts have been given like index numerals. Thus, the housing 5a has a substantially planar body portion 9, curved body portion 10, outer sealing edge 11 and a flange 6. The inner sealing edge 12a is again uniformly inset from the outer sealing edge 11 with an air space 18 therebetween. The inner sealing edge 12a constitutes a flange which depends downwardly from the inside surface of the housing portion 10. The lowermost end of the inner sealing edge 12a is beaded or rounded in the same manner as is the outer edge 11. It will be noted that once again the sealing surfaces of the edges 11 and 12a are substantially coplanar. The use of the housing 5a is identical to that described with respect to housing 5.

Another embodiment of the housing of the present invention is illustrated in FIG. 8. In this Figure, the housing is indicated at 5b. The housing 5b is substantially identical to the housing 5a of FIG. 7, and again like parts have been given like index numerals. The embodiment 5b of the housing differs from the embodiment 5a only in the provision of a plurality of spikes 19. Three such spikes 19 are shown in FIG. 8. Each spike 19 constitutes an integral, one-piece part of the housing structure. The spikes 19 are directed inwardly of the housing 5b and their purpose is to engage and retain the absorbent pad 7 (see FIGS. 2 and 5), when used. The housing 5b will be provided with a plurality of such spikes evenly spaced along the inner sealing edge 12a. While the number of such spikes does not constitute a limitation on the present invention, it has been found that four such spikes will generally serve the purpose.

Yet another embodiment of the housing of the present invention is illustrated at 5c in FIG. 9. The embodiment 5c is substantially identical to the embodiment 5b and again like parts have been given like index numerals. Thus, the embodiment 5c has a substantially planar body portion 9, a downwardly and outwardly curved portion 10, sealing edge portions 11 and 12a separated by air space 18, a flange 6, and a first set of inwardly directed spikes 19 identical to spikes 19 of FIG. 8. The embodiment 5c differs from the embodiment 5b in that a second set of inwardly directed spikes 20 is provided. Three such spikes are shown in FIG. 9. Each spike 20 is spaced inwardly from the inner sealing edge 12a and depends downwardly from the inside surface of the planar portion 9. The pointed end of each spike 20 extends inwardly of the structure.

The purpose of spikes 20 is to serve as additional means to engage and retain the absorbent pad 2 (see FIG. 5). While the number of spikes 20 is not a limitation on the present invention, excellent results have been achieved with four such spikes 20, evenly spaced about the center of the structure, and offset 45° with respect to the spikes 19, as shown in FIG. 9. In all other respects, the use of the embodiment 5c is identical to that described with respect to the embodiment 5.

FIGS. 10 and 11 are fragmentary cross sectional views illustrating chambers provided with flanges according to the present invention, but having only one continuous, skin-contacting edge. To this end, the chamber embodiment 5d of FIG. 10 is identical to embodiment 5 of FIG. 4 with the exception that the inner skin-engaging edge 12 has been eliminated. The chamber 5d comprises an integral, one-piece molded structure of an inverted, circular, dish-shaped configuration. The chamber 5d has a substantially planar central portion 9, a downwardly and outwardly curved portion 10 terminating in the beaded or rounded skin-contacting edge 11, and the substantially planar flange 6. The use of housing 5d and the material from which it is molded are the same as described with respect to the embodiment 5 of FIGS. 2-5. It is within the scope of the invention to provide the embodiment 5d with an internal outer array of spikes 19, as taught with respect to FIG. 8, or an outer array of spikes 19 and an inner array of spikes 20, as taught with respect to FIG. 9.

The embodiment 5e of FIG. 11 is again substantially identical to the embodiment 5 of FIGS. 2-5, differing only that the outer skin-contacting edge 11 has been eliminated. Thus, the chamber 5e comprises an integral, one-piece, molded structure of an inverted, circular, dish-shaped configuration. The chamber 5e has a substantially planar central portion 9. Near its periphery, the chamber 5e has a portion 10 which curves downwardly and outwardly and which terminates in a skin-contacting edge 12 comprising a laterally and inwardly extending annular flange-like portion 14 with a relatively wide, flat, annular skin-contacting surface 15. The portion 14 can also serve as a retaining means for an absorbent pad (not shown) if desired. The embodiment 5e is provided with a planar flange 6 identical to flange 6 of embodiment 5 of FIGS. 2-5. The use of chamber 5e and the material from which it is made are the same as described with respect to the embodiment 5 of FIGS. 2-5.

The housings of the present invention are re-usable under many circumstances. Absorbent pads 7 of various diameters can be used in the same housing. It is also within the scope of the invention to produce the housing of the present invention in various sizes.

In the above description and in the claims, the housing and its parts are described using words and phrases such as "inverted", "upwardly", "downwardly", "downwardly and outwardly", and the like. It will be understood that such words and phrases are used for purposes of explanation and clarity in conjunction with the figures. In use, the housing may be placed in, or may assume, any appropriate orientation.

Modifications may be made in the invention without departing from the spirit of it.

What is claimed is:

1. A patch system for use on the skin of a human or animal subject for predictive testing, diagnostic testing and to serve as a dermal delivery system for drugs, said patch system comprising an open, one-piece, inverted dish-shaped housing of non-toxic, inert, soft and flexible material, said housing terminating about its periphery in at least one continuous skin-contacting edge, a substantially planar flange extending outwardly from the exterior of said housing and being spaced slightly upwardly from said at least one continuous skin-contacting edge, said outwardly extending flange having a bottom surface, a layer of pressure-sensitive adhesive on said flange bottom surface, whereby said adhesive-coated flange affixes said housing to the skin.

2. The patch system claimed in claim 1 wherein said housing terminates in two parallel, spaced, continuous skin-contacting edges, said two skin-contacting edges lying in the same plane, said outwardly extending flange lying in a plane parallel to and spaced slightly upwardly from said plane of said skin-contacting edges.

3. The patch system claimed in claim 2 wherein said outwardly extending flange comprises an integral, one-piece part of said housing.

4. The patch system claimed in claim 3 wherein said housing is circular, said outwardly extending flange comprising a continuous annular flange.

5. The patch system claimed in claim 2 including an absorbent pad located within said housing.

6. The patch system claimed in claim 5 including a removable release paper covering said housing, said pad and said adhesive coated outwardly extending flange.

7. The patch system claimed in claim 2 including a removable release paper covering said housing and said adhesive coated outwardly extending flange.

8. The patch system claimed in claim 2 wherein said housing is circular, said outwardly extending flange comprising a continuous annular flange.

9. The patch system claimed in claim 8 wherein said flange has a width equal to at least one third the diameter of said housing and a thickness not greater than one-half the wall thickness of said housing.

10. The patch system claimed in claim 1 wherein said outwardly extending flange comprises an integral, one-piece part of said housing.

11. The patch system claimed in claim 10 wherein said housing is circular, said outwardly extending flange comprising a continuous annular flange.

12. The patch system claimed in claim 1 including an absorbent pad located within said housing.

13. The patch system claimed in claim 12 including a removable release paper covering said housing, said pad and said adhesive coated outwardly extending flange.

14. The patch system claimed in claim 1 including a removable release paper covering said housing and said adhesive coated outwardly extending flange.

15. The patch system claimed in claim 1 wherein said housing is circular, said outwardly extending flange comprising a continuous annular flange.

16. The patch system claimed in claim 15 wherein said flange has a width equal to at least one third the diameter of said housing and a thickness not greater than one-half the wall thickness of said housing.

* * * * *